(12) United States Patent
Sogaro

(10) Patent No.: US 8,100,597 B2
(45) Date of Patent: Jan. 24, 2012

(54) ARRANGEMENT FOR APPLYING A LIQUID

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 901 days.

(21) Appl. No.: 11/995,280

(22) PCT Filed: Jul. 12, 2006

(86) PCT No.: PCT/EP2006/006829
§ 371 (c)(1),
(2), (4) Date: Jun. 6, 2008

(87) PCT Pub. No.: WO2007/009649
PCT Pub. Date: Jan. 25, 2007

(65) Prior Publication Data
US 2011/0150559 A1    Jun. 23, 2011

(30) Foreign Application Priority Data

Jul. 15, 2005   (EP) .................................... 05015477

(51) Int. Cl.
*A46B 11/00* (2006.01)

(52) U.S. Cl. ............................. 401/44; 401/47; 401/151

(58) Field of Classification Search ................... 401/44, 401/47, 151; 222/81, 82, 86, 137, 145.5, 222/145.6; 604/140, 191
See application file for complete search history.

(56) References Cited

U.S. PATENT DOCUMENTS

| | | | |
|---|---|---|---|
| 4,741,737 A | 5/1988 | Meyer et al. | |
| 6,059,570 A | 5/2000 | Dragan et al. | |
| 6,447,476 B1 | 9/2002 | Sogaro | |
| 6,450,810 B1 | 9/2002 | Fischer et al. | |
| 6,719,729 B2 * | 4/2004 | Sogaro | 604/191 |
| 2002/0160333 A1 | 10/2002 | Pierson et al. | |

FOREIGN PATENT DOCUMENTS

| | | |
|---|---|---|
| DE | 4418682 A1 | 11/1995 |
| EP | 1205196 A | 5/2002 |
| FR | 1262088 A | 5/1961 |

OTHER PUBLICATIONS

PCT/EP2006/006829 International Search Report dated Dec. 7, 2006.

* cited by examiner

*Primary Examiner* — Tuan Nguyen
(74) *Attorney, Agent, or Firm* — Quarles & Brady LLP

(57) ABSTRACT

The invention relates to a device for applying a fluid, comprising an application container (12) limiting a receiving space (34), the application container being equipped at a first end (14) with an application unit (16), and being connected via a valve unit (20) at a second end to a reservoir container (22) having a reservoir space (38), the reservoir container being embodied of a sleeve which is guided at a plunger-like cylindrical body (26) of the valve unit (20) via an annular collar (24) that has a lateral channel (30), which is connected to an axial channel (32), which leads to the receiving space (34) of the application container (12). The reservoir container (22) is detachably embodied as opposed to the application container (21) such that in a closed position of the reservoir container (22) a fluid flow between the reservoir space (38) of the receiving space (34) is blocked, and that in an activating position of the reservoir container (22) the reservoir space (38) and the receiving space (34) are connected via the lateral channel (30) and the axial channel (32).

9 Claims, 1 Drawing Sheet

ARRANGEMENT FOR APPLYING A LIQUID

CROSS REFERENCE TO RELATED APPLICATIONS

Figures 1, 2:
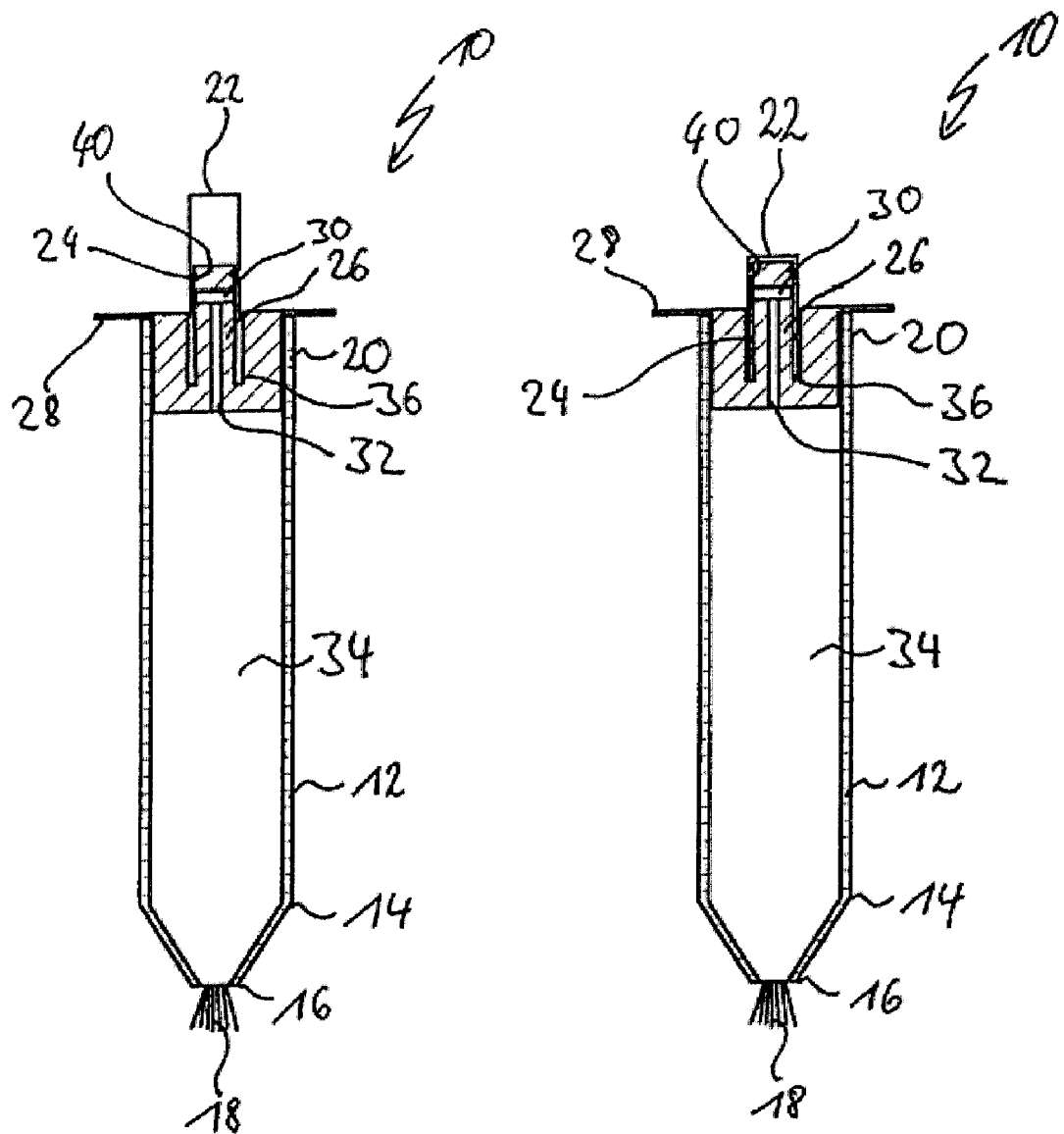

This application represents the national stage application of International Application PCT/EP2006/006829, filed 12 Jul. 2006, which claims the benefit of EP Patent Application 05015477.2, filed 15 Jul. 2005, which is incorporated herein by reference in its entirety for all purposes.

The invention relates to a device for applying a fluid.

Devices of many different types for applying a fluid are known in practice, and are, for example, embodied as a syringe type, during the actuation of which a plunger presses onto a fluid reservoir contained within a cylindrical hollow space such that the fluid is discharged via a nozzle.

Furthermore, a so-called mini-syringe is known in practice, which essentially has a cylindrical syringe body, at the first front face of which an application device in the form of a brush, a pipet syringe, or such, is embodied, and at the second front face of which a sleeve-type reservoir container is arranged, which is closed on the side facing away from the application device, and which is guided at a plunger-type cylindrical body of the syringe body via a sealing annular collar protruding from an inner wall of the reservoir container. The plunger-type cylindrical body comprises a crosshole in the area of the reservoir container, from which a longitudinal bore is branched, leading to the application device. When the annular collar encompasses the cylindrical body upstream, i.e. at the side of the lateral channel facing away from the application device, the flow of a fluid between the reservoir container and the application device is blocked. If pressure is applied to the reservoir container in the direction of the application device such that the reservoir container is displaced as opposed to the syringe body, the annular collar of the reservoir container glides over the lateral channel. By means of the pressure applied by the cylindrical body onto the fluid contained in the reservoir container, the fluid is transported via an annular gap between the cylindrical body and the side wall of the reservoir, as well as the lateral channel and the longitudinal channel to the application device. This mini-syringe, however, is suited only for one-component systems.

The invention is based on the task of creating an application device, which provides a broad range of applications for applying fluids.

In order to solve this task, a device for applying a fluid is provided according to the invention, which comprises a tube-like application container limiting a receiving space, the application container being equipped at a first end with an application device, and at its second end being connected via a valve unit to at least one reservoir container having a reservoir space. The reservoir container is embodied from a sleeve, which is closed on the side facing away from the application device, and which is guided via at least one sealing annular collar radially protruding from an inner wall of the sleeve, at a plunger-like cylindrical body of the valve unit. The cylindrical body has a lateral channel in the area of the sleeve, which is connected to a longitudinal channel leading to the receiving space of the application container. The reservoir container is movably embodied against the application device such that in a closed position of the reservoir container the flow of a fluid between the reservoir space of the reservoir container and the receiving space of the application container is blocked, and in an activated position of the reservoir container the receiving space and the reservoir space are connected to the valve unit via the axial channel and the lateral channel.

The device according to the invention can be utilized in many ways, and can, for example, be utilized for applying multi-component fluids, wherein a component of the reservoir space of the reservoir container, and the other component are received by the receiving space of the application container. When activated, i.e. upon pressure applied to the reservoir container, after moving a certain distance, the flow of fluid is released between the reservoir space and the application container such that components of a multi-component system can be mixed in the application container.

The components of a multi-component system can be either separated in the reservoir container and the application container before activation of the device according to the invention, or they can also be stored in chambers of the reservoir containers that are separated by at least one partition wall. In the latter case the partition wall is displaced upon activation of the device such that all components are displaced in the receiving space of the application container, and can be mixed therein before application.

In order to prevent the components from discharging from the device before they are mixed it is purposeful if a detachable or a releasing locking device is provided in the area of the application device.

In a special embodiment of the device according to the invention the application container is made of an elastic, deformable soft plastic material. For the application, lateral pressure can then be manually applied onto the application container such that the fluid contained therein is discharged via the application device.

In order to facilitate the activation of the device according to the invention, an actuating flange is preferably embodied in the area of the second end of the application container. Two fingers of a user's hand, for example, can engage into the actuating flange therewith, while the thumb of the same hand presses against the free and closed front end of the reservoir container for activation, whereby the fluid contained in the reservoir container is transported into the application container via the valve unit.

In order to be able to completely discharge the reservoir container, the plunger-like cylindrical body purposefully has a length essentially corresponding to the axial extension of the reservoir container. The cylindrical body can therewith dip to the bottom of the reservoir container into the same, and displace the fluid from the reservoir container.

Preferably, the plunger-like cylindrical body is limited by an annular recess of the valve unit, into which the reservoir container dips upon the displacement in the activated position.

In order to define a locking position of the reservoir container, the annular collar of the reservoir container can cooperate with an annular groove of the cylindrical body, which is arranged upstream of the lateral channel.

The application device can be embodied in manifold form that is adjusted to the respective application. For example, the application device comprises a brush, a nozzle, and/or a sponge-like application device.

Further advantages and advantageous embodiments of the object according to the invention are obvious from the description, the drawing, and the patent claims.

One embodiment of the device according to the invention is schematically illustrated in the drawing in a simplified version, and is explained in further detail in the description below. It shows:

FIG. 1 a longitudinal section across an application device for a multi-component agent in the deactivated position; and FIG. 2 the device according to FIG. 1 in the activated position.

The drawing illustrates an application device 10, which can, for example, be utilized in medicine for applying a two-component system. For example, the device 10 can be utilized in dentistry for the placement of a ceramic inlay, or such, for applying an adhesive, or such.

The device 10 comprises an application container 12, which is embodied in the shape of a tube, and is made of an elastic, deformable soft plastic material. At a first end the application container 12 is equipped with an application unit 16, which in this case is embodied having a brush-like element 18.

At the side facing away from the application unit 16, a so-called valve unit 20 is inserted in the application container 12, which connects the application container 12 to a reservoir container 22 illustrated in a reverse cup shape in the present illustration. The reservoir container 22 is made of an elastic, deformable plastic material, and is embodied in the style of a sleeve that has a sealing annular collar 24 at its inner wall, via which it is guided in an axially sliding manner at a plunger-like cylindrical body 26 of the valve unit 20. The reservoir container 22 is closed at the end facing away from the application container 12.

The plunger-like cylindrical body 26 comprises in an area protruding over an actuating flange 28 a lateral channel 30, which is connected to an axial channel 32, which leads to an inner space 34 of the application container 12.

Furthermore, the valve unit 20 has an annular recess 36, which encompasses the plunger-like cylindrical body 26, and into which the reservoir container 22 dips at its side wall.

In order to define a closed position, in which the flow of a fluid between a reservoir space 38 of the reservoir container 22 and the receiving space 34 of the application container 12 is blocked, the cylindrical body further has upstream of its circumference an annular groove 40, i.e. illustrated in the drawing as being above the lateral channel 30, which cooperates with the annular collar 24 of the reservoir container 22. In the closed position the annular collar 24 engages into the annular groove 40.

In the deactivated position illustrated in FIG. 1, a first component of a multi-component system in powder or liquid form is contained in the receiving space 34 of the application container 12. The reservoir space 38 of the reservoir container 22 contains a second fluid component of the multi-component system.

By means of the annular collar 24 adjacent to the cylindrical body 26, engaging into the annular groove, it is avoided that the fluid contained in the reservoir space flows into the receiving space 34 of the application container 12.

When the device 10 is activated, an axial pressure is applied to the reservoir container 22 in the manner of activating a ball point pen, whereby the reservoir container 22 is displaced as opposed to the application container 12 in the direction of the receiving space 34, and the annular collar 24 crosses over the openings of the lateral channel 30. Due to the force applied by the plunger-like cylindrical body 26, the fluid is displaced in the reservoir space 38 across an annular gap between the side wall of the reservoir container 22 and the cylindrical body 26, the lateral channel 30, and the axial channel 32 into the receiving space 34 of the reservoir container 12. There, the fluid is mixed with the other component. The reservoir container 22 is pressed into the direction of the application container 12 until the free front face of the cylindrical body 26 stops at the bottom of the reservoir container 22. Thus, the nearly complete discharge of the reservoir container 22 occurs.

After the mixing of the two components in the receiving space 34 of the application container 12 has taken place, a locking device, which is not illustrated in detail, can be released, and the two-component system can be applied onto a respective location by means of lateral manual pressure via the application device 16 and its brush insert 18, which is not attached until this time.

In one embodiment that is not illustrated in detail, the reservoir container has two reservoir spaces arranged successively in axial direction, which a separated by means of a moveable partition wall, and in which one component each of a multi-component system is arranged. When this system is activated, i.e. upon axial pressure applied onto the reservoir container, initially that component, which is contained in the reservoir space directly adjacent to the cylindrical body, is displaced into the receiving space of the application container. Once the free front face of the cylindrical body then stops at the partition wall between the two reservoir spaces, the discharging of the second reservoir space begins by means of displacement of the partition wall in axial direction such that the component contained in this second reservoir space is also displaced into the receiving space of the application container, and is mixed with the first component.

The invention claimed is:

1. A device for applying a fluid, said device comprising:
a tube-like application container having a receiving space for mixing fluid components, said container extending between a first end and a second end;
an application unit disposed at said first end downstream of said receiving space;
a valve unit upstream of said receiving space and having a valve body disposed at said second end and in fluid communication with said receiving space, said valve body including a plunger-like cylindrical body extending away from said application unit; and
a reservoir container having at least one reservoir space connected to said valve unit, the reservoir container including a sleeve closed at a side facing away from the application unit, and which is guided at the plunger-like cylindrical body of the valve unit via an annular collar that protrudes at least radially from an inner wall of the sleeve, the cylindrical body having a lateral channel that is arranged in the area of the sleeve, and that is connected to an axial channel, which leads to the receiving space of the application container through said valve body, wherein the reservoir container is movable between a closed position and an activating position, such that in the closed position of the reservoir container a fluid flow between the reservoir space of the reservoir container and the receiving space of the application container is blocked by said annular collar, and that in the activating position of the reservoir container the reservoir space and the receiving space are connected via the lateral channel and the axial channel of the valve unit, wherein the application container is made of an elastic, deformable soft plastic material, and the plunger-like cylindrical body of the valve unit is limited by an annular recess of the valve unit, into which the reservoir container dips upon the displacement in the activating position.

2. The device according to claim 1, wherein an actuating flange is arranged in the area of the second end of the application container.

3. The device according to claim 1, wherein the plunger-like cylindrical body has a length essentially corresponding to the axial extension of the reservoir container.

4. The device according to claim 1, wherein the definition of the closing position of the reservoir container the annular collar cooperates with an annular groove, which is arranged upstream of the lateral channel at the circumference of the cylindrical body.

5. The device according to claim 1, wherein the application device comprises a brush.

6. The device according to claim 1, wherein the application device comprises a nozzle.

7. The device according to claim 1, wherein the application device comprises a sponge-like application device.

8. The device according to claim 1, wherein the receiving space of the application container receives a first mixing component, and the reservoir space of the reservoir container receives a second mixing component of a two-component system, which is mixed with the first mixing component upon a displacement of the reservoir container in the activated position into the receiving space of the application container.

9. The device according to claim 1, wherein the reservoir container has several reservoir spaces, which are separated from each other by means of at least one moveable partition wall.

* * * * *